United States Patent
Shubat et al.

(10) Patent No.: US 11,472,722 B2
(45) Date of Patent: Oct. 18, 2022

(54) WATER ENERGY MATRIX CONTROL

(71) Applicant: SPI Technology Ltd., Ottawa (CA)

(72) Inventors: James Shubat, Ottawa (CA); Gerben Op Den Buijs, Veldhoven (NL); Ludo Feyen, Heusden-Zolder (BE)

(73) Assignee: SPI Technology Ltd., Ottawa (CA)

( * ) Notice: Subject to any disclaimer, the term of this patent is extended or adjusted under 35 U.S.C. 154(b) by 170 days.

(21) Appl. No.: 16/971,768

(22) PCT Filed: Feb. 28, 2019

(86) PCT No.: PCT/CA2019/050240
§ 371 (c)(1),
(2) Date: Aug. 21, 2020

(87) PCT Pub. No.: WO2019/165552
PCT Pub. Date: Sep. 6, 2019

(65) Prior Publication Data
US 2021/0070635 A1    Mar. 11, 2021

Related U.S. Application Data

(60) Provisional application No. 62/637,358, filed on Mar. 1, 2018.

(51) Int. Cl.
*C02F 1/50* (2006.01)
*C02F 1/72* (2006.01)
*E03B 7/07* (2006.01)

(52) U.S. Cl.
CPC ............... *C02F 1/50* (2013.01); *C02F 1/722* (2013.01); *C02F 2209/02* (2013.01);
(Continued)

(58) Field of Classification Search
CPC ........ C02F 1/50; C02F 1/722; C02F 2209/02; C02F 2209/06; C02F 2209/36;
(Continued)

(56) References Cited

U.S. PATENT DOCUMENTS 6,393,775 B1 * 5/2002 Staschik ................. F02G 1/043
210/241
9,188,363 B2   11/2015 Buescher et al.
(Continued)

FOREIGN PATENT DOCUMENTS

DE    102012002152 A1    8/2013
JP       2010243200 A   10/2010
(Continued)

OTHER PUBLICATIONS

Machine-generated English translation of DE102012002152, dated Apr. 12, 2022.*
(Continued)

*Primary Examiner* — Fred Prince

(57) ABSTRACT

A system and method for controlling microbiological growth in a water system and premise plumbing system which uses stabilized hydrogen peroxide as a disinfectant and maintains water energy matrix control. Maintenance of stable hydrogen peroxide residual in the system in combination with active temperature monitoring enables better control of the water energy matrix and reduction of hot water temperature while maintaining microbiological control.

15 Claims, 8 Drawing Sheets

(52) U.S. Cl.
CPC ...... *C02F 2209/06* (2013.01); *C02F 2209/36* (2013.01); *C02F 2209/40* (2013.01); *C02F 2303/04* (2013.01); *C02F 2307/14* (2013.01); *E03B 7/074* (2013.01)

(58) Field of Classification Search
CPC .............. C02F 2209/40; C02F 2303/04; C02F 2307/14; E03B 7/074; Y02A 20/20; Y02B 30/18; G01N 33/1826; E03C 1/044; F24D 17/001; F24D 17/0078
USPC ....... 210/739, 742, 758, 759, 764, 774, 175, 210/198.1, 205
See application file for complete search history.

(56) References Cited

U.S. PATENT DOCUMENTS

| | | | |
|---|---|---|---|
| 9,835,601 B2 | 12/2017 | Shubat et al. | |
| 10,132,510 B2 | 11/2018 | Heil et al. | |
| 10,317,381 B2 | 6/2019 | Shubat et al. | |
| 2005/0000911 A1* | 1/2005 | Thorpe | C02F 1/325 210/748.12 |
| 2012/0279929 A1* | 11/2012 | Daniels | F24D 17/0031 122/13.01 |
| 2017/0158537 A1 | 6/2017 | Buschmann | |
| 2017/0305768 A1 | 10/2017 | Shubat et al. | |
| 2018/0024574 A1* | 1/2018 | Goodjohn | F24H 9/2007 700/300 |

FOREIGN PATENT DOCUMENTS

| | | |
|---|---|---|
| JP | 5857739 B2 | 7/2013 |
| WO | 2009036032 A1 | 3/2009 |
| WO | 2009036054 A1 | 3/2009 |

OTHER PUBLICATIONS

Machine-generated English translation of JP2013139951, dated Apr. 12, 2022.*
Martin et al., Antibacterial Properties and Mechanism of Activity of a Novel Silver-Stabilized Hydrogen Peroxide, PLOS ONE, Jul. 8, 2015, 1 0(7).
Shuval et al., An innovative method for the control of legionella infections in the hospital hot water systems with a stabilized hydrogen peroxide-silver formulation, International Journal of Infection Control, Apr. 2009, vol. 5, Issue 1.
Casini, et al., Application of hydrogen peroxide as an innovative method of treatment for Legionella control in a hospital water network, Pathogens, 2017, vol. 6, Issue 1 5, pp. 1-12, doi: 10.3390.

* cited by examiner

| Floor | Room | Fixture | Baseline - cATP (pg/ml) | | | | | |
|---|---|---|---|---|---|---|---|---|
| | | | Week 1 | Week 3 | Week 5 | Week 49 | Week 94 | Week 96 |
| 1 | Mechanical Room | Municipal water supply in | 0.42 | 0.68 | 0.18 | 4.59 | - | 0.24 |
| | | SPI Sample valve | | | | | 0.17 | |
| | Floor 1 Shower Room | Shower – cold | 0.45 | 0.82 | 0.11 | 0.36 | - | 0.58 |
| | | Shower – hot (t = 60 s) | 0.4 | 3.2 | 0.2 | 0.51 | - | 0.11 |
| | 1102 | Sink (mixer tap) | 1.08 | 11.71 | 2.75 | 37.95 | - | 8.56 |
| | Floor 1 Ladies Room near Mechanical Room | Sink (mixer tap) | - | - | - | - | 0.03 | - |
| 2 | 2206 | Shower – cold | 0.5 | - | 0.16 | 0.46 | - | 2.11 |
| | | Shower – hot (t = 0 s) | 1.18 | - | 0.52 | 1.03 | - | 10.57 |
| | | Shower – hot (t = 60 s) | 0.97 | 1.46 | 0.12 | 0.48 | - | 0.27 |
| | Ladies Washroom | Sink (mixer tap) | - | - | - | - | 0.05 | - |
| 3 | 3175 | Shower – cold | 1.34 | 0.84 | 0.14 | 1.24 | - | 0.33 |
| | | Shower – hot (t = 0 s) | 1.25 | 0.57 | 0.09 | 0.46 | - | 0.16 |
| | | Shower – hot (t = 60 s) | 1.62 | 0.7 | 0.12 | 1.41 | - | 0.11 |
| | 4175 | Shower – cold | 2.4 | 0.94 | 1.66 | 1.07 | - | 0.86 |
| | | Shower – hot (t = 0 s) | 2.77 | 5.48 | 0.29 | 0.97 | - | 1.35 |
| | | Shower – hot (t = 60 s) | 2.94 | 3.1 | 0.45 | 0.86 | - | 0.2 |
| 4 | 4501Q | Sink – cold | 3.52 | 1.03 | 1.17 | 3.24 | - | 1.23 |
| | | Sink – hot (t = 0 s) | 4.43 | 5.81 | 4.75 | 68.18 | - | 8.76 |
| | | Sink – hot (t = 75 s) | 1.37 | 4.87 | 4.01 | 70.92 | - | 3.35 |
| | Ladies Washroom | Sink (mixer tap) | - | - | - | - | 0.17 | - |

Figure 5

| Floor | Room | Fixture | Week 3 | | Week 49 |
|---|---|---|---|---|---|
| | | | T°C | pH | T°C |
| 1 | Mechanical Room | Municipal water supply in | 13.6 | 8.90 | 7 |
| | Floor 1 Shower Room | Shower – cold | 14.0 | 8.40 | 8 |
| | | Shower – hot (t = 60 s) | 48.0 | 8.70 | 55 |
| | 1102 | Sink (mixer tap) | 34.7 | 8.60 | 23 |
| 2 | 2206 | Shower – cold | 14.0 | 8.70 | 9 |
| | | Shower – hot (t = 0 s) | 42.0 | 8.60 | - |
| | | Shower – hot (t = 60 s) | 44.8 | 8.00 | 53 |
| 3 | 3175 | Shower – cold | 14.8 | 8.00 | 12 |
| | | Shower – hot (t = 0 s) | 39.7 | 8.30 | - |
| | | Shower – hot (t = 60 s) | 40.7 | 8.30 | 44 |
| 4 | 4175 | Shower – cold | 24.4 | 7.80 | 14 |
| | | Shower – hot (t = 0 s) | 32.8 | 8.60 | - |
| | | Shower – hot (t = 60 s) | 42.9 | 8.30 | 44 |
| | 4501Q | Sink – cold | 23.0 | 8.60 | 22 |
| | | Sink – hot (t = 0 s) | 30.7 | 8.20 | - |
| | | Sink – hot (t = 75 s) | 31.0 | 8.40 | 30 |

Figure 6

| Time | HW Temp (°C) | $H_2O_2$ (mg/l) | CFU/l *<br>Shower 1 | CFU/l *<br>Shower 2 |
|---|---|---|---|---|
| Baseline | 48 – 55 | 8 | >20,000 | 200 |
| Week 1 | 42 | 7.1 | <100 | <100 |
| Week 2 | 48 | 7.7 | <100 | <100 |
| Week 4 | 45 | 7.2 | <100 | <100 |
| Week 8 | 38 | 7.8 | <100 | <100 |
| Week 12 | 40 | 7.2 | <100 | <100 |

*Legionella pneumophila Serotype 2-

Figure 7

WATER ENERGY MATRIX CONTROL

CROSS REFERENCE TO RELATED APPLICATION

This application claims priority to Provisional U.S. Ser. No. 62/637,358 filed on Mar. 1, 2018, and is a United States National Stage application under 35 U.S.C. 371 of PCT Application No. PCT/CA2019/050240, filed on 28 Feb. 2019, the content of both of which is hereby incorporated by reference in their entirety.

FIELD OF THE INVENTION

The present invention pertains to control of the water energy matrix in a premise plumbing system. The present invention also pertains to an apparatus, system and method for controlling microbiological growth in a premise plumbing system using stabilized hydrogen peroxide as a disinfectant.

BACKGROUND

Opportunistic pathogens in premise plumbing systems pose a significant risk to human health. In premise plumbing systems with hot water lines or circulating hot water, conditions in the plumbing system can be opportune for microbiological growth such that water already treated with primary disinfection has insufficient residual disinfectant to control pathogen growth, which increases risk of user exposure and infection. Premise plumbing in large buildings poses a unique challenge in that distribution lines can be long, and systems have a multitude of distal outlets that are generally unmonitored for microbiological growth. Requirements for heated water at remote lines without secondary disinfectant also provides an opportunity for opportunistic microbiological growth. Purpose-built water systems such as cooling towers, HVAC systems, evaporative condensers, pools, spas, and other locations of stagnant water in a plumbing system can also provide favourable conditions for growth of opportunistic microorganisms. Risk assessment and continuous monitoring of institutional, residential and commercial water supplies is critical to ensure water safety and provide risk mitigation of opportunistic pathogens in premise plumbing and purpose-built water system.

The bacterium *Legionella* spp. is one opportunistic pathogenic bacterial species common in natural water sources such as rivers, lakes, ponds, and reservoirs. Microorganisms such as *Legionella* can also survive in a wide range of natural and artificial environments and can be active, grow, and be pathogenic under favourable growth conditions. *Legionella* also demonstrates resistance to chemical agents such as chlorine at concentrations usually applied for water disinfection in potable water systems. In addition, *Legionella* can shelter in biofilms, and free-living protozoa, especially cysts, can protect the bacteria against disinfectants. *Legionella pneumophila* contamination of hot water systems is particularly difficult to control due to fact that hot water systems, which usually operate at 40-50° C., provide the optimal growth conditions for *Legionella*. In addition, the presence of biofilm, sludge, scale, corrosion, deposits of water hardness such as calcium and magnesium, and water pipe and conduit fouling provide ideal nutrient and growth conditions for *Legionella* bacteria and cysts of amoebic trophozoite which harbour *Legionella* bacteria. Biofilms can also harbour other multiple species of opportunistic pathogenic bacteria and protozoan species, creating cysts and protective structures which are difficult to penetrate and can release and repopulate downstream. *Legionella* is dormant below 20° C. and does not survive above 60° C., which is why many government building standards require water heaters to be maintained at or above 60° C. to discourage microbiological growth. At water temperatures above 45-50° C., however, there is a serious danger of scalding to users. In addition, a lot of energy is required to heat and maintain the temperature of hot water heaters above 60° C. In premise plumbing systems with long water lines and where there is high heat loss, hot water temperatures must be maintained even higher to prevent biofilm growth in hot water lines far from the water heating system.

Chlorine is a powerful disinfectant and very effective against a broad range of waterborne pathogens, particularly under conditions where there is a maintenance of chlorine residual in the distribution system. Chlorine is commonly used as a systemic chemical disinfectant in potable water plumbing systems, with treatment of water commonly carried out at centralized municipal water treatment centres. The most active disinfectant species of chlorine is hypochlorous acid (HOCl), however hypochlorous acid is unstable in water, particularly at high temperature and high pH. A serious drawback of chlorine disinfection also includes the production of disinfectant by-products such as trihalomethanes (THMs) and haloacetic acids, many of which are known to be biotoxic. Chloramines are weaker oxidants than chlorine, resulting in fewer regulated by-products, however their use results in increased incidence of corrosion of lead and copper plumbing systems, further providing favourable growth conditions for microbiological organisms. In particular, a pH below 7.0 in the presence of chlorine creates highly corrosive water, whereas a pH above approximately 7.8 to 8.0 greatly diminishes chlorine's disinfectant efficacy. Available corrosion control techniques can be used including pH adjustment, alkalinity adjustment, and addition of corrosion inhibitors. However, for hard, alkaline water, pH and alkalinity adjustment is not an option because excessive precipitation of calcium carbonate can occur and diminish the hydraulic capacity of the pipes. Orthophosphate can be used as a corrosion control chemical for hard, alkaline water, however stringent phosphorus discharge limits at municipal wastewater treatment and copper corrosion limit the amount of orthophosphate that can be added to water.

Stagnation of water in drinking water distribution systems can result in increased level of trace metals in the water, including lead and copper. Metal leaching frequently occurs when chlorine is present in acidic water environment. Due to these reasons, flushing is commonly employed to keep the water moving in order to reduce chlorine contact time and maintain the lead and copper concentration within Health Guidelines. However, this approach has the major drawbacks of wasting water and energy.

Secondary disinfection can be used to treat water already treated by a primary disinfectant or water that already has a low microbiological load. In particular, stabilized hydrogen peroxide (SHP) has been used as a secondary disinfectant in municipal water supplies to preserve the integrity of the water in the distribution system. Stabilized hydrogen peroxide has been extensively evaluated for use as a secondary and primary disinfectant in potable water systems, including Municipal Drinking Water Treatment Plants, Campgrounds, Farms (Dairy, Fruits and Vegetable), Food Processing Facilities, and households. Hydrogen peroxide stabilized with metal ions such as silver has particularly been found to be effective in the secondary disinfection of water in premise plumbing systems. Stabilized hydrogen peroxide is also stable in hot water and able to maintain a residual peroxide concentration in hot water to prevent possible re-contamination of water. The presence of the ionic silver in particular has been shown to enhance interactions of stabilized hydrogen peroxide with the bacterial cell surface, and the silver in stabilized hydrogen peroxide may facilitate this association through electrostatic interactions at the cell surface. (Martin et al., Antibacterial Properties and Mechanism of Activity of a Novel Silver-Stabilized Hydrogen Peroxide, *PLOS ONE*, Jul. 8, 2015, 10(7)) The long term efficacy of stabilized hydrogen peroxide disinfectant is attributable in part to the bacteriostatic effect of the small amounts of silver which deposit on the walls of the piping system or tanks, and coat sediments and biofilms. It is hypothesized that the positive metal ions bond to the negative bacterial cell walls sites, disrupting membrane structure which leads to bacterial cellular death aided by $H_2O_2$ penetration. The combined stabilized hydrogen peroxide formulation of $H_2O_2$ and silver and select other metals has been found to be some 100 times more powerful as a disinfectant than hydrogen peroxide alone and can provide a long lasting effective disinfectant residual of many days and weeks. Two tests reported in hospitals in Israel (Shuval et al., An innovative method for the control of *legionella* infections in the hospital hot water systems with a stabilized hydrogen peroxide-silver formulation, *International Journal of Infection Control*, April 2009, Vol. 5, Issue 1) and Italy (Casini, et al., Application of hydrogen peroxide as an innovative method of treatment for *Legionella* control in a hospital water network, Pathogens, 2017, Vol. 6, Issue 15, pp. 1-12, doi:10.3390) demonstrate that stabilized hydrogen peroxide can be used effectively to control *Legionella pneumophila* in hospital hot water systems. In one study of a municipal water supply system, stabilized hydrogen peroxide was able to suppress microbial activity within the distribution system at a level comparable to what was achieved with chlorine even when the microbial activity within the raw water during the SHP monitoring had doubled from the time of monitoring when chlorine was being used. This data suggests that SHP can provide microbial suppression equivalent to sodium hypochlorite and perhaps somewhat superior.

There remains a need for effective, efficient, safe, and healthy control and disinfection of opportunistic pathogens in building plumbing systems.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a system, apparatus and method for effective, efficient, safe, and healthy control and disinfection of opportunistic pathogens in building plumbing systems.

In an aspect there is provided a hot water system comprising: a water heater comprising a water heater temperature control for maintaining the water heater below a threshold temperature; a dosing apparatus for dosing hydrogen peroxide into the hot water treatment system; a measurement apparatus for measuring concentration of stabilized hydrogen peroxide in the water treatment system; and a control unit receiving the concentration of stabilized hydrogen peroxide and instructing the dosing apparatus to dose and maintain the concentration of stabilized hydrogen peroxide at a minimal threshold concentration.

In an embodiment, the system further comprises a temperature sensor downstream the water heater for monitoring temperature at a distant location in the hot water system. In an embodiment, the threshold temperature is 60° C. In another embodiment, the system further comprises an ATP sensor. In another embodiment, the system further comprises a pH sensor. In another embodiment, the system further comprises a water flow sensor. In another embodiment, the control unit further controls a hydrogen peroxide dosing pump. In another embodiment, the control unit can be accessed remotely.

In another aspect there is provided a method for water energy matrix control in a hot water system, the method comprising: monitoring concentration of hydrogen peroxide in the water system; dosing the water system with stabilized hydrogen peroxide to maintain the concentration of stabilized hydrogen peroxide at a minimal threshold concentration; and monitoring temperature in the water system to maintain the water system below a threshold temperature.

In an embodiment, the method further comprises monitoring microbiological growth in the water system. In another embodiment, monitoring microbiological growth in the water system comprises measuring concentration of cellular ATP in the water system, detection of microbiological DNA in the water system, or a combination thereof. In another embodiment, the method further comprises lowering the temperature in the water system. In another embodiment, the threshold temperature in the water system is less than 60° C. In another embodiment, the method further comprises maintaining the threshold temperature saves energy while controlling microbiological load at a safe level. In another embodiment, the method further balancing dosing stabilized hydrogen peroxide with water heating to control microbiological load. In another embodiment, the minimal threshold concentration of stabilized hydrogen peroxide is 1 ppm. In another embodiment, the method further monitoring microbiological growth at multiple locations in the water system. In another embodiment, the method further dosing the water system with additional stabilized hydrogen peroxide when microbiological growth is detected. In another embodiment, the concentration of hydrogen peroxide in the hot water system is measured accurate to 0.1 mg/L.

In another aspect there is provided a premise plumbing system comprising: a water heater with temperature controller; a dosing pump for dosing stabilized hydrogen peroxide into the premise plumbing system; an in-line apparatus for measuring the concentration of hydrogen peroxide at different locations in the premise plumbing system; a temperature sensor for measuring temperature of the water system downstream the water heater; a control system for receiving hydrogen peroxide concentration data from the in-line apparatus and controlling the dosing pump based on the hydrogen peroxide concentration in the premise plumbing system; and a network of pipes connecting the water heater, dosing pump, control system, in-line apparatus and temperature sensor, wherein the control system maintains an acceptable residual concentration of hydrogen peroxide in the premise plumbing system.

In an embodiment, the control system controls the temperature controller of the water heater such that the water heater is maintained below a threshold temperature. In another embodiment, the threshold temperature is less than 60° C. In another embodiment, the network of pipes comprises a recirculating hot water loop. In another embodiment, the system further comprises an ATP sensor. In an embodiment, the ATP sensor is an in-line sensor.

In another aspect there is provided a method for reducing energy use in a potable water premise plumbing system, the method comprising: heating the potable water with a water heater; dosing stabilized hydrogen peroxide into the premise plumbing system; periodically measuring, in-line, the residual concentration of hydrogen peroxide at at least one location in the premise plumbing system; controlling a dosing pump to maintain a minimum residual concentration of hydrogen peroxide in the premise plumbing system; and maintaining temperature of the water heater at a temperature of less than 60° C.

In an embodiment of the method, the minimum residual concentration of hydrogen peroxide in the premise plumbing system is 1 ppm. In another embodiment, the method further comprises measuring the flow rate of water in the premise plumbing system; and calculating the estimated required amount of stabilized hydrogen peroxide required to maintain a minimum residual concentration of hydrogen peroxide in the premise plumbing system based on the flow rate.

In another embodiment, the method further comprises dosing stabilized hydrogen peroxide at multiple locations in the premise plumbing system. In another embodiment, the in-line measuring of the residual concentration of hydrogen peroxide occurs at multiple locations in the premise plumbing system. In another embodiment, the method further comprises measuring microbiological load in the premise plumbing system at a location distant from the site of stabilized hydrogen peroxide dosing; reducing the temperature of the water heater; periodically remeasuring the residual concentration of hydrogen peroxide in the premise plumbing system at a location distant from the stabilized hydrogen peroxide dosing location; and remeasuring the microbiological load in the premise plumbing system at a location distant from the dosing location to ensure that microbiological growth is controlled.

In an embodiment of the method, measuring microbiological load comprises measuring the concentration of cellular ATP in the potable water. In another embodiment of the method, microbiological load is measured in-line in the premise plumbing system.

In another aspect there is provided an in-line apparatus for controlling microbiological growth in potable water in a premise plumbing system, the apparatus comprising: a measurement cell for receiving a sample of the potable water; a light transmitter configured to emit light at a selected wavelength at the measurement cell; a photodiode receiver configured to receive light passing through the measurement cell; a reagent supply comprising a reagent compound configured to react with hydrogen peroxide to form a reaction product, the reaction product adapted to absorb light at the selected wavelength proportional to the amount of hydrogen peroxide in the water sample; a supply valve for directing a potable water sample from the premise plumbing system to the measurement cell, the valve configured to provide a constant water volume to the measurement cell; a temperature sensor for measuring water temperature in the premise plumbing system; and a control unit, wherein the control unit is programmed to: control the supply valve in a time-dependent manner, cause a first colorimetric measurement of a first water sample free of reagent and a second colorimetric measurement of a second water sample mixed with reagent, determine the difference between the first and second measurements, and compare the difference against a pre-determined standard curve of diluted hydrogen peroxide to determine and report the concentration of hydrogen peroxide in the water sample.

In an embodiment of the apparatus, the concentration of hydrogen peroxide in the water sample is measured accurate to 0.1 mg/L. In another embodiment of the apparatus, the control unit further controls temperature of a water heater in the premise plumbing system. In another embodiment, the apparatus further comprises a pH sensor. In another embodiment, the apparatus further comprises a flow sensor. In another embodiment of the apparatus, the control unit further controls a hydrogen peroxide dosing pump. In another embodiment of the apparatus, the control unit can be accessed remotely. In another embodiment of the apparatus, the reagent is potassium bis(oxalato)oxotitanate (IV). In another embodiment of the apparatus, the light transmitter is a light emitting diode (LED) light emitter. In another embodiment, the apparatus further comprises an ATP sensor.

In another aspect there is provided a premise plumbing system comprising: a water heater with temperature control; a dosing pump for injecting stabilized hydrogen peroxide into the premise plumbing system; at least one in-line apparatus for measuring the concentration of hydrogen peroxide at different locations in the premise plumbing system; at least one temperature sensor for measuring temperature of the water system; a network of pipes connecting the water heater, control system, and hydrogen peroxide meter; and a control system, wherein the control system controls the dosing pump to maintain an acceptable residual concentration of hydrogen peroxide in the premise plumbing system.

In another aspect there is provided a method for reducing energy expenditure in a potable water premise plumbing system, the method comprising: heating the potable water with a water heater; dosing stabilized hydrogen peroxide into the premise plumbing system; periodically measuring, in-line, the residual concentration of hydrogen peroxide at at least one location in the premise plumbing system; controlling a dosing pump to maintain a minimum residual concentration of hydrogen peroxide in the premise plumbing system; and maintaining temperature of the water heater at a temperature of less than 60° C.

BRIEF DESCRIPTION OF THE FIGURES

For a better understanding of the present invention, as well as other aspects and further features thereof, reference is made to the following description which is to be used in conjunction with the accompanying drawings, where:

FIG. 5 is a data table showing microbiological control in an academic building retrofit;

FIG. 6 is a data table showing microbiological control in an assisted living facility building;

FIG. 7 is a graph of energy savings by temperature differential in a building hot water system.

DETAILED DESCRIPTION OF THE INVENTION

Figure 1:
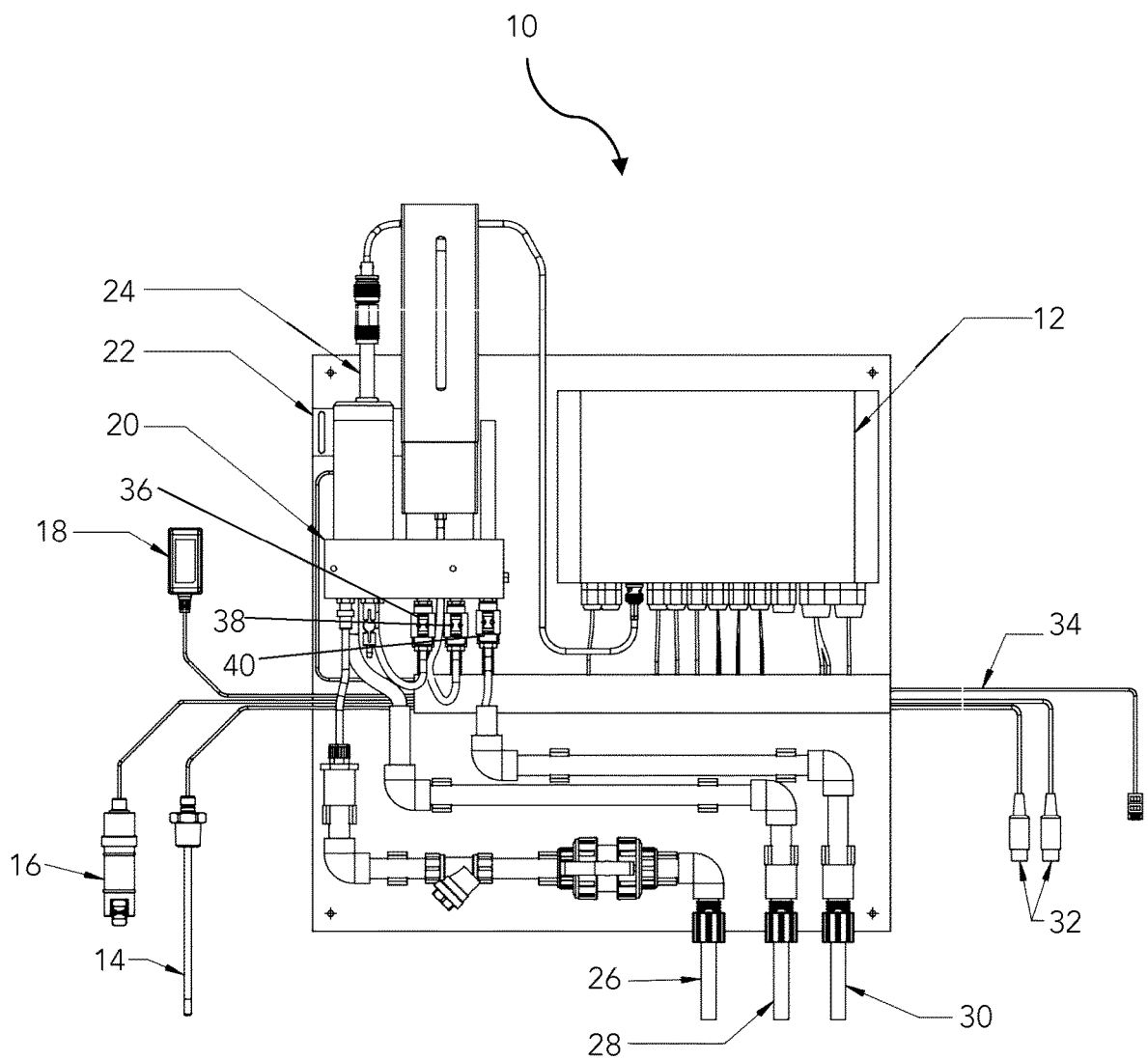
FIG. 1 illustrates a monitoring and control system for stabilized hydrogen peroxide in a plumbing system.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The term "stabilized hydrogen peroxide" as used herein refers to a solution of hydrogen peroxide in water comprising a stabilizer. A variety of stabilizers can be used, such as, for example, low concentrations of metal ions such as copper or silver. One preferable stabilizer is silver ions or silver colloid. in minute concentrations used for water disinfection, an example of which is HUWA-SAN™ manufactured by Roam Technology NV of Houthalen, Belgium which contains 0.013-0.017% ionic silver. Depending on the solution, the silver prevents the hydrogen peroxide from oxidizing too quickly when it contacts water, thereby allowing the solution to mix with the water before binding to and disinfecting undesirable microorganisms and chemicals. Preferable stabilized hydrogen peroxide solutions are stabilized by silver ions or silver colloid, also known as oligodynamic silver, in minute concentrations. Drinking water disinfection using hydrogen peroxide and silver has been approved by jurisdictions worldwide include the United States Environmental Protection Agency (USEPA), by the Drinking Water Inspectorate (DWI) in the United Kingdom, by the Ontario Ministry of the Environment, and by health authorities in Australia, among others.

The term "premise plumbing" as used herein refers to potable water plumbing systems in buildings of any size. In particular, premise plumbing includes large buildings that contain closed loop or circulating water systems, and particularly closed loop or circulating hot water systems. Types of buildings with premise plumbing or closed loop or circulating hot water systems can include but are not limited to: hotels, hospitals, schools, apartment buildings, healthcare offices and buildings, office buildings, libraries, community centres, single family houses, and the like.

The term "water energy matrix" as used herein refers to the combination of energy and water required to maintain a potable water system in a healthy condition for human consumption and use. In a potable water system, water is used for human consumption, but is also required for cleaning and flushing the system infrastructure such as pumps, pipes, filters, and the like. Energy in a potable water system is used for heating the water as well as pumping and monitoring. Where the water system infrastructure is problematic and provides loci and conditions for opportunistic pathogen growth, more water and energy are required to maintain the system in healthy form for human consumption. For environmental and financial reasons, it is beneficial to be able to limit energy and water use in a potable water treatment system while also limiting pathogen growth and providing healthy water to consumers.

Herein is described a hot water system, apparatus, system and method for water energy matrix control in water systems and premise plumbing systems. Also described is a system and method for controlling disinfection simultaneously with controlling the water energy matrix in a premise plumbing system in a building. The present invention also pertains to an apparatus, system and method for controlling microbiological growth in a premise plumbing system using stabilized hydrogen peroxide as a disinfectant.

Stabilized Hydrogen Peroxide (SHP) is a new generation of hydrogen peroxide which remains stable longer in highly diluted form and retains residual levels of active peroxide at low concentrations in many different kinds of water matrixes. SHP remains stable over prolonged retention times while enabling a targeted and controlled reaction and oxidation of organic material and target organisms. Unlike conventional hydrogen peroxide, the reaction of stabilized hydrogen peroxide is controlled and degradation more gradual, enabling much enhanced effectiveness against target micro-organisms and protection of water or wet surface integrity, in cold and warm water conditions at a wide pH range. SHP has also been found to be more effective in controlling biofilm compared to sodium hypochlorite and generic hydrogen peroxide. It has been speculated that this high killing efficacy of SHP is the result of the trace amount of silver ions, which disrupt the quorum sensing communication responsible for biofilm production (Martin N L, et al. *PLoS ONE* 10(7), 2015). In addition, it has also been hypothesized that the minute quality of silver ion in SHP assists the hydrogen peroxide target the bacterial cell surface. Bacteria, such as *Legionella*, can be challenging to kill in building plumbing systems since any biofilm can act as a highly protective shelter to protect the bacteria from chlorine disinfectants. In controlling biofilm, *Legionella* populations can also be more easily controlled.

The proven disinfection effectiveness of stabilized hydrogen peroxide based chemical disinfectants has been extended to hot water systems where it has been found that unlike chlorine, stabilized hydrogen peroxide retains significant and safe residual concentration levels during and after heating. In a premise plumbing system with chlorine as the only disinfectant, residual chlorine levels are almost undetectable after water is heated at 60° C. for 15 minutes and the high temperatures required to kill pathogenic bacteria render the chlorine in the water system less effective as a disinfectant. The implication of this instability of chlorine at high temperatures renders the water downstream the water heater largely free of effective levels of chemical disinfection in chlorine-only systems, which can result in colony formation inside the plumbing system and unacceptable levels of microbiological growth, especially at pipes and infrastructure far from water treatment or heating systems. In particular, it has been found that higher temperature accelerates the decomposition of chlorine residual in a hot water system. In contrast, the stability and disinfection efficacy of stabilized hydrogen peroxide at premise plumbing hot water temperatures reduces the need to maintain water heaters at temperatures of 60° C. (the current standard for thermal disinfection), resulting in significant cost-saving on the energy perspective and reduction in carbon emission for carbon-based energy use. Stabilized hydrogen peroxide can be successfully employed in domestic and commercial hot water circulation systems for microbiological control, specifically for *Legionella* control. Continuous monitoring and dosing of SHP also acts as a more proactive and preventive measure for *Legionella* growth compared to chlorine based methods. The standards of water heating to prevent opportunistic pathogen growth are based on chlorine disinfection water systems, and it has been found that chemical disinfection with stabilized hydrogen peroxide does not require the same high temperatures to provide equivalent elimination of opportunistic pathogens in the water system. Thus, the use of stabilized hydrogen peroxide lowers the energy and water requirements in premise plumbing systems, controlling the water energy matrix and reducing the energy and water needed to supply healthy water in buildings.

The combined formulation of $H_2O_2$ and silver and other metals has been found to be some 100 times more powerful as a disinfectant than hydrogen peroxide alone and can provide a long lasting effective disinfectant residual. In drinking water regulation, acceptable concentration thresholds for hydrogen peroxide are in the order of under 10 ppm. For example, in Ontario, Canada, operating concentrations for drinking water are between 2-8 ppm. Our studies have further shown that the SHP formulation's disinfection power also increases as water temperature increases, which contributes to its effective control of *Legionella* bacteria in hot water systems which normally operate at temperatures up to 40-60° C.

Continuous and in-line dosing and monitoring of hydrogen peroxide residual concentration in water in a premise plumbing system thus provides efficient disinfection and control of opportunistic pathogenic microorganisms in the water supply. In lieu of extensive and on-going thermal disinfection and difficult to maintain temperature control, a chemical disinfection system based on stabilized hydrogen peroxide combined with effective temperature monitoring enables continuous dosing of stabilized hydrogen peroxide into hot water systems that provides effective continuous biofilm and bacteriological control. Control of microbiological growth is more challenging in hot water systems since the elevated temperatures can provide more ideal growth environments to opportunistic pathogens, however the present apparatus and system can be effectively used in unheated or cold water systems while providing microbiological control without water heating.

Water stagnation in dead end pipes within a building distribution system can also cause problems, in particular in hot water premise plumbing with primary chlorine disinfectant, because downstream the water heater is where the lowest chlorine concentrations are. Since disinfection can still allow microbiological growth, stagnant or dead end pipes with low flow, low disinfectant concentrations, and potentially with heated water, can provide a near optimum growth environment for opportunistic pathogens. As SHP decomposes at a much slower rate compared to chlorine and is more stable at high temperature, the concentration of disinfectant in stagnant pipes can be prolonged. With controlled peroxide residual concentrations flushing can also be kept to a minimum, thereby reducing excess water flow and saving water required for system maintenance. With the use of SHP, a long-lasting disinfectant residual can thus be retained throughout the distribution network, regardless of temperature or distance from the water heater(s) or site of disinfectant dosing.

Compared to conventional disinfection regime using chlorine and chlorine based products, stabilized hydrogen peroxide is biodegradable and does not produce harmful disinfection by-products including trihalomethanes (THMs) and haloacetic acids (HAAs), whose long term exposure are strongly correlated to increase in some cancers. This further avoids the need of flushing the water distribution system in order to maintain disinfection byproducts below the regulation limit and thereby limits the amount of flushing water required to maintain in the water system. Stabilized hydrogen peroxide has also been shown to have the capacity to treat and control biofilm caused by bacteria including *Legionella pneumophila* and *Pseudomonas aeruginosa*.

One method of measuring opportunistic pathogen load in a plumbing system involves sampling and analysis of potable water at various points throughout the building for adenosine triphosphate concentrations, temperature, and pH. Other methods include water sampling and PCR testing to quantify and identify the pathogenic load in the water supply. The results of these analyses lead to recommendations on corrective actions necessary for ensuring a safe supply of potable water. Adenosine triphosphate (ATP) is a substance which is the energy source for the living cells found in every organism and is used by living cells as a co-enzyme or unit of chemical energy and only found in association with living cells. Detection of ATP concentrations indicates the presence and extent of the biological community in a sampled water source and can be used to identify water that has been in contact with biofilms and could potentially be harboring harmful pathogens such as *Legionella*. Cellular ATP (cATP) represents the ATP generated by living microorganisms suspended within a liquid and is directly related to the planktonic population. Periodic testing for ATP and temperature monitoring on hot and cold sides of a premise plumbing building system help to ensure biofilm control and microbiological risk mitigation. Previous studies have shown that ATP correlates with other microbial tests (e.g. heterotrophic plate counts) and therefore, the ATP test is an attractive option for drinking water facilities when an estimation of the microbial loading in a sample is required. As a result, measurement of ATP concentrations (via an ATP test) in a sample provides an indirect measurement of both the health and the concentration of the biological community. The benefit of an ATP test to more traditional microbial tests is that the ATP test provides a rapid indication of the microbial concentration of a water sample. Location or spot testing for cATP can be done. Preferably the control unit of the peroxide monitoring apparatus is connected to an in-line system for periodic or continuous monitoring of cATP concentration such that sudden spikes in ATP, indicative of a sudden increase in microbial growth, can be managed quickly by increasing dosing of SHP into the system. One example of an ATP monitoring system is a test kit and luminometer available from LuminUltra® which is based on the reaction of ATP with oxygen and luciferin in the presence of luciferase which produces detectable light. In one ATP monitoring system, a semi-automatic digital meter can be used. In another, an integrated automated system can be configured to send a signal to the control unit or external controller.

Other than lowering energy requirement for thermal disinfection in a chlorine-based disinfection system, reduction of the amount of chlorine in the plumbing system leads to less corrosion to the distribution network and prevention of iron, copper and lead leaching from the pipes. Compared to chlorine-based disinfectants, stabilized hydrogen peroxide and peroxide based chemicals are less corrosive. In anaerobic environments, the presence of iron reducing bacteria (IRB) contributes to iron and steel pipe corrosion as the result of reduction of insoluble ferric ion compounds to soluble ferrous ion compounds. This reaction leads to the removal of protective corrosion products formed on exposed iron alloy surfaces. It has been reported that IRB are also involved in biofilm formation and act to set up differential electrical cells which promote corrosion. Different from chlorine-based disinfectants, SHP treated drinking water has higher oxygen content and oxidizing peroxide radicals. As facultative anaerobes, IRB shifts to aerobic respiration when oxygen is available. Therefore, the use of SHP disinfection may also alleviate pipe corrosion by providing more oxygen to the water, further extending the lifetime of pipes, conduits, and equipment. The estimated expenditure for replacing existing corroded water distribution piping is $1.5 billion dollars. (Informing the Future: The Canadian Infrastructure Report Card® 2016) A recent global investigation on drinking water distribution pipelines suggest the Netherlands has the best drinking water distribution pipes in terms life-span in the world, with one of the main reasons attributed that the Netherlands does not use chlorine as their primary or second disinfectant. Hence, significant cost savings can be gained on capital and maintenance cost as the reduction or absence of chlorine will prolong pump and piping lifespan. Further, biofilms can contribute to piping surface degradation, and the elimination of biofilm with the exposure of continual low-concentration stabilized hydrogen peroxide reduces bacterial biofilm-caused pipe and part corrosion.

FIG. 1 illustrates a monitoring and control system apparatus for stabilized hydrogen peroxide in a plumbing system. The apparatus 10 measures the concentration of hydrogen peroxide in a water system in a continuous or in-line system to provide safe and continuous disinfection control. The apparatus comprises control unit 12 capable of receiving input data from sensors and direct output control of one or more dosing pumps, temperature controllers, pH pumps, and other devices. The control unit 12 can have built-in proportional integral feedback loops, for both $H_2O_2$ and pH control, with the capability of providing, either via 4-20 mA or pulse output, a signal to one or more dosing pumps to control dosing of stabilized hydrogen peroxide into the system. There are two different types of signals that can be relayed to and from a controller to a piece of equipment, or vice versa (i.e. flow meter, dosing pump, etc.). The information can be passed by either an analog signal, or a digital (also known as pulse) signal. Pulse signals essentially relay a binary signal (on/off, yes/no, 1/0). Analog signals are smooth signals that vary over time, that use either direct current ("DC") or alternating current ("AC") to communicate data. Some controllers can send and receive both types of signals, while some can only send or receive one type. A signal transducer must be used to convert one type of signal to the other if the equipment and controller do not communicate using the same type of signal. The most common analog signal range for a controller or piece of equipment is 4-20 milliamps ("mA") DC, 0-5 Volts ("V") DC or 0-10V DC. This represents 0-100% of the process available (i.e. if dosing pump is desired to dose 4 LPH at the maximum, and 0 LPH at the minimum, a set point of 4 mA would correspond to 0 LPH and 20 mA would be 4 LPH, and as the pump operates a calculation can be done to the percentage the pump is running at). In this way the measured variable concentration of peroxide can be maintained as close as possible to the set point.

Temperature in a premise plumbing system is measured by the apparatus in conjunction with the peroxide measurement to provide effective disinfection and temperature control throughout the system. The temperature sensor 14 can be configured to take the water temperature at or after the water heater as well as on the return lines to determine what the return temperature and disinfectant levels are at that moment to ensure water is safe. Temperature and peroxide levels can also be measured on the cold water line to ensure safe water quality with sufficient peroxide residual. The minimum required hydrogen peroxide residual concentration on the hot water return line is 1 ppm, and the minimum suggested hydrogen peroxide residual concentration is 2 ppm on the cold water line. A flow sensor 16 measures water flow in the premise plumbing system and estimates the dosing amount of stabilized hydrogen peroxide required to provide adequate disinfection and residual peroxide concentration in the system. The peroxide measurement unit 20 is capable of reading $H_2O_2$ residual concentration in the water using a colorimetric assay. The peroxide measurement unit 20 uses a colorimetric assay based on production of a reaction product that absorbs light at a selected wavelength and can provide continuous readings to an accuracy of to 0.1 mg/L (0.1 ppm). The measurement chamber inside the peroxide measurement unit 20 comprises a light source to emit light at a selected wavelength, a measurement cell, and a photodiode receiver. In one embodiment, the hydrogen peroxide measurement unit 20 comprises a measurement cell with a width of 10 mm, a cell wall thickness of 1 mm, and a cell height of 19.5 mm. A measurement cell of these dimensions can hold a sample volume of about 2 mL. Other volumes are also contemplated. These parameters were selected as optimal dimensions for this embodiment given a number of factors including sufficient sample size for greatest accuracy and precision, as well as cost. The material used for the measurement cell should be selected based on light transmission capabilities and resistance to degradation from water, water components, and chemical reagents. All channels can further be polished to a high transparency level to maximize light transmission. The measurement cell can further be polished on the inside to enable maximum light transmission. The size and design of the measurement cell will influence the accuracy and efficiency of the measurement. Factors may include, but are not limited to, the path length from a light emitter to a light receiver, the light yield of the light source and the sensitivity of the light receiver, the measurement cell composition and cell wall thickness, and distance between emitter and receiver elements. The physical parameters such as measurement cell wall thickness, path length and photodiode emitter and receiver equipment are fixed once chosen and therefore can be compensated by hardware calibration and system settings. In a preferred embodiment, measurement cell can be custom milled from a single piece of thermoplastic polycarbonate, such as Lexan™, with known techniques such as a CNC mill station.

Formation of the reaction product between the reagent and the peroxide is proportional to the amount of hydrogen peroxide in the water sample. In one preferable embodiment the reagent compound is potassium bis (oxalato) oxotitanate (IV). The reagent mixture can also comprise one or more of the following compounds: potassium bis (oxalato) oxotitanate (IV) DI (Merck KGaA, Darmstadt, Germany); EDTA di-sodium salt dihydrate Titriplex III™ (Merck KGaA, Darmstadt, Germany); Surfactant: Polyoxyethylene (23) lauryl ether Brij™ 35 (30%) (Sigma-Aldrich); dissolved in a solvent of sulfuric acid 99%: p.a. 10% solution (Merck KGaA, Darmstadt, Germany). The wavelength for the emitter is selected to correspond with the selected reagent. Preferably the light emitter comprises a LED light. In one reagent and emitter combination, the selected of the emitter is wavelength is 470 nm. In another embodiment the reagent comprises potassium bis (oxalato) oxotitanate (IV) DI, EDTA di-sodium salt dihydrate and polyoxyethylene (23) lauryl ether mixed in a solvent. In one embodiment the solvent is sulfuric acid 99%: p.a. 10% solution. In a further embodiment the predetermined standard curve comprises data points from 0 ppm to 150 ppm. In another embodiment the predetermined standard curve comprises data points from 0 ppm to 100 ppm. Quantification of the reaction product is measured and converted to a peroxide concentration based on a standard curve. Additional details on the peroxide measurement unit 20 can be found in the inventors' U.S. Pat. No. 9,835,601 B2 granted on Dec. 5, 2017, incorporated herein by reference.

The apparatus can further comprise one or more pH sensor 24 to provide an indication of pH at different points along the water flow path. Water supply 26 is connected to the plumbing water supply in the premise plumbing system and draws a sample of potable water at a site in the apparatus. Water reservoir level sensor 22 measures the amount of water in the hydrogen peroxide measurement unit 20, which can comprise of a buffer jar with a constant volume, as determined by a water reservoir level sensor 22 and adjusted by an overflow tube 28. Measurement water disposal 30 is the outlet of measurement water mixed with reagent from the peroxide measurement unit 20. The peroxide measurement unit 20 can further have control cables 32 for controlling pH and disinfectant dosing pumps and a network cable for 34 remote access. A power adapter 18 provides power connection to the apparatus.

The present apparatus can be installed at a single place or multiple places in the premise plumbing system depending on the building size, microbiological load, age, type of plumbing, use, or history of microbiological growth. Installation of two or more apparatuses placed strategically in the premise plumbing system can allow the multiple apparatuses to work in concert to provide overall system stability in terms of constant monitoring of water temperature and residual disinfectant concentration. Where microbiological loads are problematic, more regular monitoring, more apparatuses, and additional dosing is recommended.

For the apparatus to measure peroxide concentration in the water, light is transmitted through the walls of a measurement cell containing the sample and the resulting non-absorbed light is captured on a photodiode. A small current is generated in the photodiode, which is measured by an operational amplifier and converted by an analog/digital (AD) convertor to an internal value of 1000, which is the resolution of the measurement processor. This is the null value or zero reagent sample. A preferred colorimetric method is based on production of a reaction product that produces a yellow to orange coloured complex when potassium bis(oxalato)-oxotitanate (IV) reacts with hydrogen peroxide to form a reaction product adapted to absorb light at 470 nm proportional to the amount of hydrogen peroxide in the sample. Quantification of the reaction product is measured at 470 nm and converted to a $H_2O_2$ concentration based on a calibration curve. The photodiode measurement data produced by the reaction product of the above reactant with $H_2O_2$ has been determined to correlate logarithmically with $H_2O_2$ concentration. Alternatively, other wavelengths may be used such as 400 nm. The wavelength that gives the maximum absorbance of the coloured reaction product is one consideration in choosing a selected wavelength. Additionally the resulting standard curve and degree of linearity that can be achieved may vary at each wavelength. In one embodiment of the present invention, the wavelength is selected to be 470 nm. The standard curve generated with this data produces a close to linear standard curve and a high degree of accuracy is thereby achieved.

Prior to use, the apparatus 10 is calibrated. Samples having known concentrations of hydrogen peroxide are measured and a standard curve is created by plotting the observed measurement cell output signal measurement against the known concentration. This curve can be represented graphically or by mathematical extrapolation. The concentration of hydrogen peroxide in an unknown sample is then determined with reference to the standard curve and the result reported, displayed or recorded either digitally, graphically or by other convenient means. Preferably, the standard curve includes a range of known samples spanning the range of concentrations to be measured, for example from 0-150 mg/L (ppm). The standard curve comprising data points in the desired range (i.e. 0-150 mg/L) greatly increases the accuracy of the determination and is key to providing an accuracy of 0.1 mg/L. Calibration and use of a standard curve to calculate concentration of hydrogen peroxide would be known to a skilled person and is more thoroughly described in Applicant's U.S. Pat. No. 9,835,601, incorporated herein by reference.

In practice, the apparatus 10 draws a first water sample from the supply valve 36 which directs a potable water sample from the premise plumbing system to the measurement cell in the peroxide measurement unit 20. The supply valve 36 is configured to provide a constant water volume to the measurement cell. In one embodiment the supply valve 36 can be connected to a buffer jar. The buffer jar serves as a reservoir from where a water sample can be directed through the supply valve to the measuring cell at a desired time interval. Water reservoir level sensor 22 measures the water level in the buffer jar. The peroxide measurement unit 20 can further comprise an overflow tube 28 to return water to the system, thereby maintaining a constant volume in the buffer jar and a turn-over of water in the buffer jar. Water exiting the supply valve may first pass through a filter to remove particulate matter. Optionally a filter may be installed prior to water entering through the supply valve or in such other locations as to prevent or limit particulate matter from entering apparatus 10. Sample water flow is directed to the measurement cell under control of a supply valve 36, and reagent is directed to the measurement cell under control of a reagent valve. A drain valve operates to control fluid retention in, or draining of, the measurement cell. Outflow from the measurement cell is directed to a water disposal 30. The measurement cell has an upper opening and a lower opening. The lower opening is connected to a network of piping to allow filling and emptying of the measurement cell with sample water and reagent as required. The upper opening of the measurement cell can be connected to a riser tube which extends upward to at least the height of the water level in the buffer jar. The riser tube increases the efficiency of rinsing the measurement cell by providing added volume and force of the water movement. Plumbing connects the elements to provide a conduit for fluid flow. For example, a first network of pipes connecting the source water to the optional buffer jar or directly to the supply valve 36, the supply valve 36 to the measurement cell, and a second network of pipes connecting the reagent vial to the reagent valve 38, the reagent valve 38 to the measurement cell, the measurement cell to the drain valve 40, and the drain valve 40 to a measurement water disposal 30. The plumbing in the apparatus can be composed of PVC piping, or flexible tubing such as Tygon™ tubing, a combination thereof, or other such conduit material as desired.

Sample water is directed into a measurement cell to determine a null or background reference measurement, removes the first sample, draws an aliquot of reagent from a reagent vial into the measurement cell and draws a second water sample from the buffer jar into the measurement cell to determine a sample measurement. The null measurement is subtracted from the sample measurement and the difference value is interpreted relative to a standard curve for a determination of hydrogen peroxide concentration. A standard curve can be represented graphically or by mathematical expression of the curve. The mathematical expression is useful in a digital system. Accuracy is provided by facilitating the closest possible adherence to the Lambert Beer principles of light absorption between the transmitter and receiver. In one embodiment, the apparatus 10 receives water from a system through the supply valve, draws a first water sample from the supply valve into a measurement cell to determine a null or background reference measurement, removes the first sample, draws an aliquot of reagent from a reagent vial into the measurement cell and draws a second water sample from the supply valve into the measurement cell to determine a sample measurement.

Figure 2:
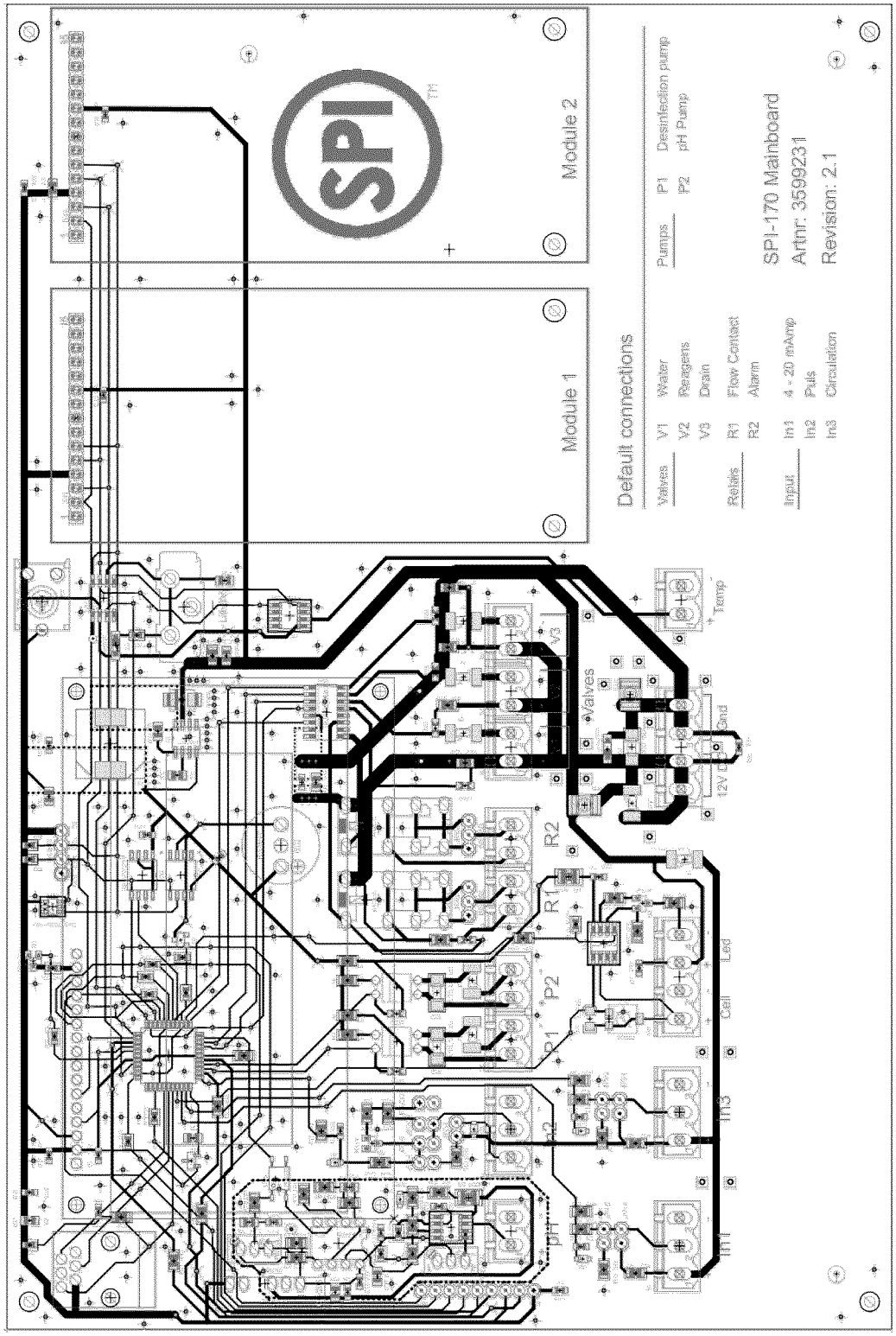
FIG. 2 is a schematic of a circuit board for the control unit in the monitoring apparatus.

FIG. 2 is a schematic of a circuit board for the control unit in the monitoring apparatus. The control unit converts signals received from different process equipment into information. The control unit can also have an attached display screen such that a mA control signal reading from a pump can be converted into a percentage or other unit so the operator knows what values the pump and other peripherals is running at. The display screen can also provide other data such as apparatus and system updates on measured values such as peroxide residual concentrations at a plurality of locations, pH at a plurality of locations, temperature at a plurality of locations, among other values.

The controller can be controlled remotely by connection to a wifi or modbus or TCP-IP or other internet connection module. A user interface can report system status and provide remote access to the premise plumbing system apparatus or multiple apparatuses and the respective control units. Data can also be obtained from the controller and displayed live and/or transmitted to other control systems by, for example by analog 4-20 mA signal or 0-10V signal. The control unit can be used to remotely monitor and report settings, for example water quality, temperature, and disinfectant concentration. The user interface can also be used to modify control unit settings remotely such as pressures and flows, pump speeds, and valve opening times. Other water quality parameters and systems can be connected and remotely controlled, such as, for example, pH detection and other chemical and flow adjustment systems. Reporting of water quality can be provided via connection of the control unit to a data stream optionally displaying on a local or remote system such as a graphical user interface, accessible by app, internet, direct or remote login, or a combination thereof. Data can be displayed by graph to analyze functioning of the premise plumbing system. Other data formats can be provided on the display or at the graphical user interface such as trend lines and long range reporting, which can be of assistance in tracking system peroxide, cATP and temperature levels over time and making appropriate adjustments as well as predictions for future usage. For example, downward drift of measurement cell null values can be indicative of system performance and can suggest, for example, contamination of the measurement cell, poorer quality incoming water, or local sites of increased microbiological loads which may require additional treatment or remediation. The control unit or additional processing device connected to the control unit can also be configured to communicate with remote devices such as smartphones or by electronic communication such as text, email, message, or other medium to report to system operators on the health of the premise plumbing system. This is especially beneficial in an emergency situation where the control unit detects a reduction in peroxide levels in the system to below a standard set point, a temperature reduction below a set point, or a measured rise in cATP above an acceptable level.

Figure 3:
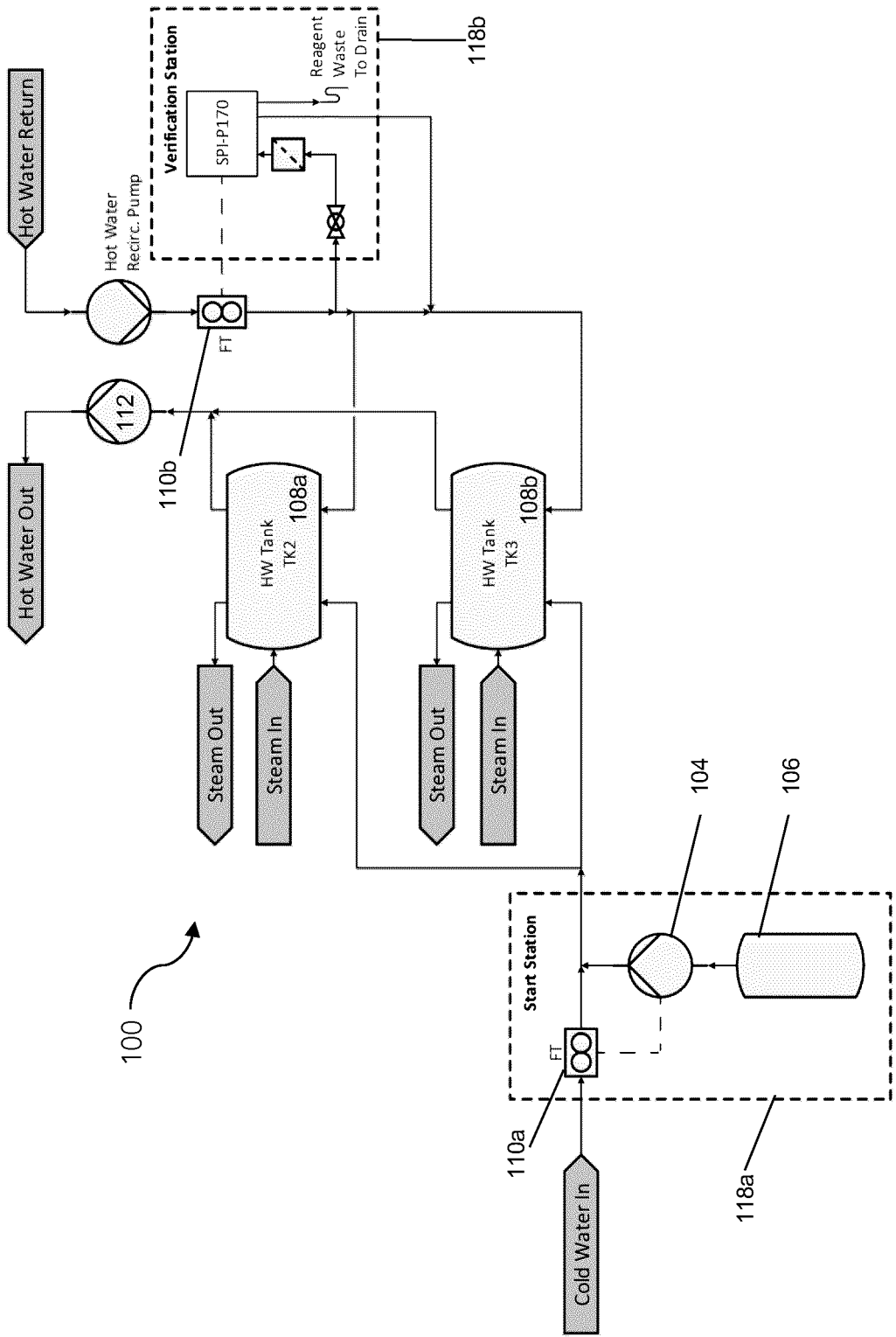
FIG. 3 is a schematic of a circulating hot water system using a stabilized hydrogen peroxide control system.

FIG. 3 is a diagram of a circulating hot water system 100 using a stabilized hydrogen peroxide control system. The system shown has a peroxide measurement apparatus 118a at the inlet of the cold water and a second peroxide measurement apparatus 118b at the hot water return, connected to a network of pipes, conduits, equipment and plumbing. One or more dosing pump 104 is attached to the premise plumbing system to provide a stable residual concentration of hydrogen peroxide in the hot water system 100. The one or more dosing pump 104 can dose the hydrogen peroxide at a number of different locations depending on the plumbing system in the building. As shown in FIG. 3, a single peroxide dosing pump 104 connected to a hydrogen peroxide reservoir 106 can be connected at the cold water intake site to provide a base level of peroxide disinfectant to the incoming water. Incoming cold water into a building can be from an underground natural water supply such as an aquifer or well, or from a municipal water supply that has already had some treatment, such as filtration and disinfection. A flow meter 110a adjacent the cold water intake detects water flow into the system, and the control unit receiving the flow rate calculates the amount of stabilized hydrogen peroxide required to be dosed by the one or more dosing pumps to provide the desired residual concentration in the system. Dosing pump 104 then doses stabilized hydrogen peroxide into the water supply from SHP reservoir 106. A variety of pumps are available, and most can be used for dosing. One common type of pump used for dosing is a "positive displacement pump," however a variety of other pumps can be used such as centrifugal pumps which are more appropriate for very large scale applications where flow rates are very high. Other commonly used pumps include peristaltic or lobe pumps, diaphragm pumps, rotary pumps, screw pumps, reciprocating pumps, centrifugal pumps, and jet pumps. Any other positive displacement pump could also be used.

The cold water is then diverted to send part of the stream to a first hot water tank 108a and a second hot water tank 108b for heating water both to steam and to supply the hot water system. A single hot water tank or more than two hot water tanks may also be connected in a similar system, with premise plumbing design based on building requirements and properties. A hot water circulation pump 112 circulates hot water to the building. As the dwell time of hydrogen peroxide in hot water is long, the peroxide residual concentration in the circulating hot water system and the microbiological load can be maintained at an acceptable level regardless of the temperature of the water heater(s). A hot water recirculation pump 114 brings water back from the peripheral pipes. A second flow meter 110b provides information on the volume or flow rate of hot water returning. A peroxide measurement apparatus 118b at the hot water return measures the residual concentration of hydrogen peroxide in the hot water return and a control unit in the measurement apparatus 118b can send a control signal to the dosing pump 104 to control the dosing rate of stabilized hydrogen peroxide into the system to maintain the concentration at a desired level. One or more additional dosing pumps can be added to the system adjacent the hot water return or elsewhere in the premise plumbing system as required to provide stable residual peroxide levels in the water supply. The control unit in the measurement apparatuses 118a and 118b also measures the temperature of the returning hot water and can be configured to control the temperature of each of the hot water tanks. Hot water returning is recirculated to the hot water tanks 108a, 108b, which mixes with cold water originating from the cold water inlet. An ATP measuring device (not shown) can be further connected to either or both of the peroxide measurement apparatus to measure ATP levels in water at the cold water inlet, the hot water return, or somewhere else in the system so that peroxide levels can be adjusted as required to control microbial growth.

Figure 4:
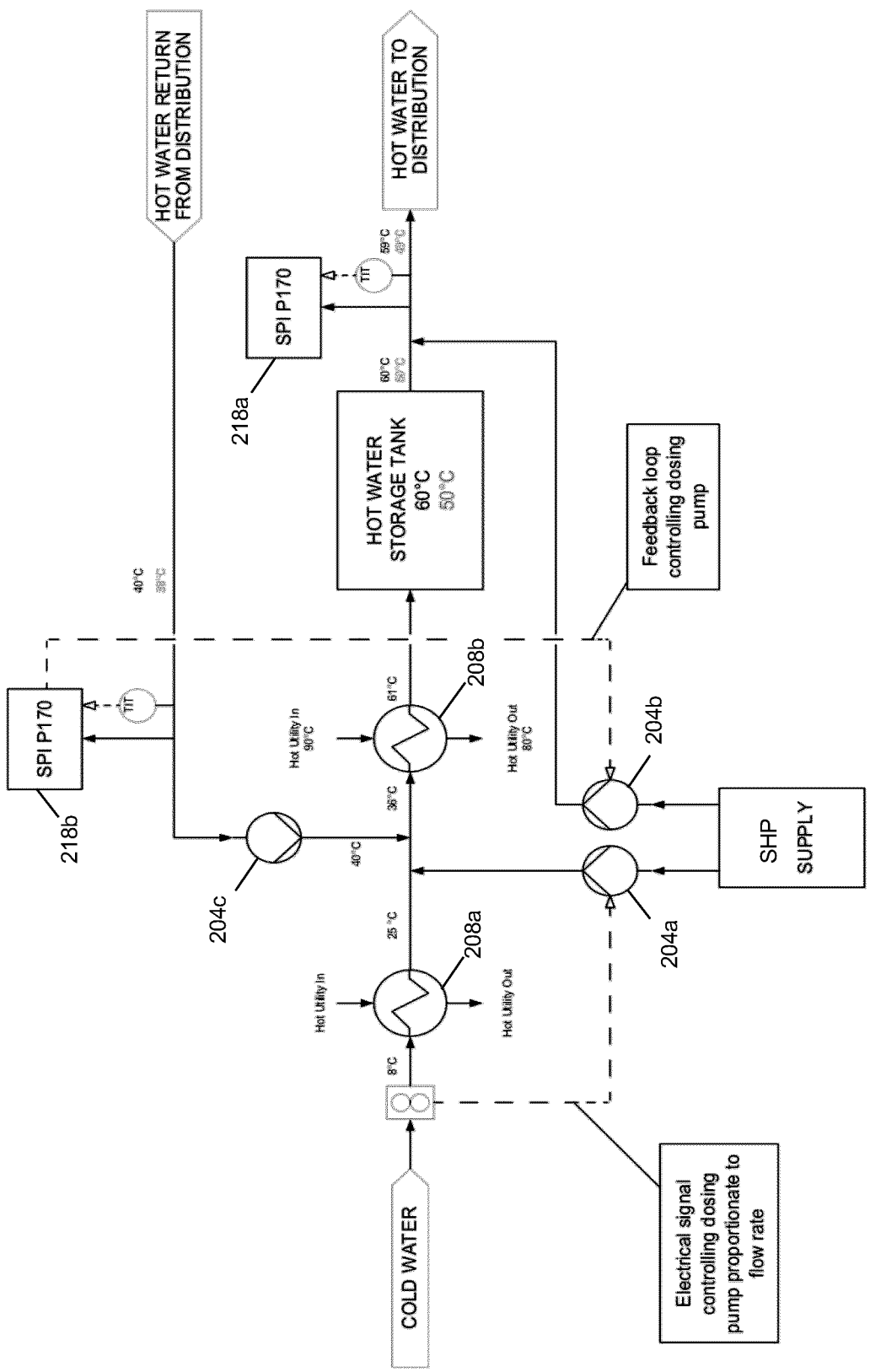
FIG. 4 is a diagram of a hot water circulation system using a stabilized hydrogen peroxide control system showing temperature differentials.

FIG. 4 is a diagram of a hot water circulation system using a stabilized hydrogen peroxide control system showing temperature differentials. In the example premise plumbing system shown in FIG. 4, a system with a hydrogen peroxide secondary disinfection system can be installed in a building which already comprises temperature and/or chlorine disinfection means for disinfecting water. Replacing high temperature disinfection with peroxide chemical disinfection allows lowering of hot water tank temperatures, however these adjustments of the hot water in the boiler must happen in such a way that both ATP and peroxide residuals levels show optimal control of water quality and biofilm.

SHP concentration in solution has been found to decrease slightly at room temperature in the presence of free chlorine. This is attributed to the quenching of the free chlorine supported by the decrease in free chlorine concentrations of the test water in the presence of SHP at room temperature. Experience in domestic hot water systems has demonstrated that SHP remains stable up to 60° C. but that the stability is influenced by dosing rate, time, and the presence of biofilm or other organic matter that may consume the SHP. When SHP was heated in the chlorinated municipal tap water, the final concentration of SHP decreased. This decrease is presumed to be related to the presence of free chlorine in the water and or other tap water constituents that expressed a higher peroxide demand upon heating.

Water temperatures at different locations in the hot water circulation system are shown in FIG. 4. In this system, water heaters 208a and 208b are shown in series, with water heater 208a heating cold water from the cold water inlet up from 8° C. to 25° C., and second water heater 208b heating the output from the first water heater 108a to from 36° C. to 61° C. Between the two water heaters hot water from the hot water return is mixed with warm water from the first water heater. Dosing pumps 204a, 204b and 204c are positioned at various places in the hot water system to dose SHP as required to maintain a safe residual concentration of hydrogen peroxide in the system. Peroxide measurement apparatuses 218a and 218b periodically monitor temperature and peroxide concentration at various places in the hot water system for the same reason.

With stabilized hydrogen peroxide capable of controlling microbial growth in the hot water system, the energy burden of heating water to kill opportunistic pathogens in the system is lessened and the role of the water heater shifts to serving to provide heated water to user outlets. The temperature differential of the water heaters and hot water storage tank can be lowered from 60-61° C. to 50° C., which provides a significant energy savings. Close monitoring of water temperature by the measurement apparatuses 218a and 218b further enables better control on temperature throughout the system to optimize energy efficiency and reduce potential harm from scalding. Water from distribution returns at a temperature of 38° C. and is also tested in line for peroxide residual concentration to provide an indication of microbial load in the system, as decreases of peroxide in the water supply can be indicative of increased requirement for microbial oxidation. Additional information can also be obtained from ATP testing which is a close proxy of microbial load. Measurement at the measurement apparatus 218a and 218b directs further dosing of SHP into the water system.

In advance of the installation of a new premise plumbing system using stabilized hydrogen peroxide as a disinfectant, flushing of the system is highly recommended, especially in cases of known excessive microbiological load and in problem or remote areas. Remediative disinfection of an existing hot water system can be carried out with at least 200 ppm of stabilized hydrogen peroxide and a dwell time of 4-6 hours after which the system should be flushed to ensure return to normal peroxide levels. The hot water heater and other appliances and equipment is also preferably disinfected with similar concentration of peroxide solution to ensure that as much biofilm in the system is eradicated as possible. Dead legs or dead ends in the pipe-work should also be identified and flushed out if possible to clean the system of any existing biofilm. Little used outlets including showerheads and taps, especially at dead legs, should be cleaned and de-scaled to further control microbiological growth in the system and to check for debris or corrosion. Additional measures are recommended to ensure that microbiology growth is minimized in premise plumbing systems. If necessary, descaling or replacement of fixtures may be necessary. Hot and cold water supplies should also be well isolated from each other with proper insulation and/or re-positioning.

EXAMPLES

Example 1—Academic Building Retrofit

A risk assessment was done of the potable water supply at a four-floor academic building. The academic building is a mixed-use laboratory and classroom building with a small area for food services as well as study and meeting rooms. The building has an estimated yearly hot water consumption of 5400 m³/year. A schematic of the circulating hot water system in the academic building is shown in FIG. 3.

FIG. 5 is a data table showing microbiological control before and after the retrofit. Weeks 1-49 were monitoring weeks wherein the building was on a standard system with incoming municipal water pre-treated with chlorine and a standard circulating hot water system with no secondary disinfectant. Having been made aware of certain risks and possible solutions, the operators installed a water disinfection system to protect the water quality and reduce the risk of *Legionella*. Post retrofit data wherein the presently described hydrogen peroxide dosing and monitoring and temperature monitoring apparatus were installed and is shown as weeks 94 and 96 in the last two columns of the table in FIG. 5.

Microbiological load was measured by concentration of cATP in the water in pg/mL. A measurement considered zero cATP is water of very good bacteriological quality with no presence of biofilm (0-0.5 pg cATP/ml). When light biofilm formation is present the concentration of cATP in the water system will be in the range of 0.5-10 pg/mL, and preventative action is recommended to get biofilm growth under control and prevent further growth. cATP levels of higher than 10 pg/mL indicate active biofilm formation present in the system and corrective action is needed to remediate the water supply to limit exposure risk. In extreme cases of severe infection the concentration of cATP in the system can be 50 pg/mL or higher, which presents a significant risk to users of exposure to *Legionella* and other opportunistic pathogens.

Based on the measurements taken at the academic building prior to retrofit it was clear that corrective action was needed to ensure continuous delivery of safe, potable hot and cold water. In particular, week 49 was in the spring when levels of organic materials in the water supply can be higher than at other times in the year. When the incoming water supply contains high levels of dissolved organics, this provides food for opportunistic pathogens in the building water supply which promotes microbiological growth, observed through a spike in cATP measurements at this time. At locations in the building far from the hot water heater where water temperatures may be lower and conduits less frequently used, such as room 4501Q on the fourth floor of the building, microbial growth levels can be dangerously high. A recommendation of requirement for a retrofit to control microbiological growth in the system was based on cATP, temperature measurements and visual inspection, which were indicative of an elevated risk of biofilm and potential opportunity for *Legionella* growth and exposure. In such building systems that have high amounts of microbiological growth, remediative disinfection of the hot water system including the water heater(s) is particularly recommended.

To remediate the building, a first stage, initial shock dose of stabilized hydrogen peroxide was used which provided a 500 ppm concentration of $H_2O_2$ to the system. After a few hours this initial shock dose was totally flushed out of the system. Shower heads, hot water faucets and other end-of-the-line plumbing fixtures were disinfected in 4% $H_2O_2$ solutions of the formulation. No residual odour or taste problems were evident as occurs when high doses of chlorine are used for similar shock disinfection.

The results of ATP sampling and analysis at the academic building are presented in FIG. 5. Samples were taken from both hot and cold water taps on three dates at various points throughout the academic building. Concentration results for ATP prior to retrofit suggest that light biofilm is present in the plumbing system at several points within the building. Results of ATP concentrations higher than 0.5 pg/ml require that preventative action be taken to lower microbial count in the system. The measurements prior to retrofit indicate the presence of biofilm, considered severe at ATP levels of >10 pg/mL. Results within this range indicate that immediate corrective action must be taken to lower microbiological load. The worst results were from the "Room 1102—sink" sampling point. This location was a water tap in a washroom that may have been subject to contamination from sources other than *Legionella*. This contamination could have raised the cATP concentration independent of any influence from the plumbing system itself. When a further sample was taken at the same point on a later date, cATP concentration had returned to within the range indicating light biofilm present.

A closer examination of the cATP results shows concentrations increasing as distance increases along the plumbing system from the hot water boiler. Values of cATP on Floor 1 were low relative to other sampling points. Concentrations then trended upwards as samples were taken on progressively higher floors. The highest cATP concentrations were generally associated with samples taken on the fourth floor at the furthest point along the plumbing system. This trend could be indicative of increased accumulation of biofilm in areas of the plumbing system furthest away from the boiler. This could also be due to temperatures moving within the range of optimal biofilm growth, increased time within piping allowing further growth, or decreasing effectiveness of residual chlorine as water moves through the plumbing system. Subsequent to retrofit, it was found that by maintaining a residual concentration of peroxide over time in both hot and cold water supplies showed a significant decrease of cATP concentration in the water supply at all locations the system.

Temperature and pH measurements taken at the academic building on are shown in FIG. 6, which is a table of temperature and pH measured in weeks 3 and 49 prior to building retrofit. Locations where the measured temperature was in the optimal microbiological growth zone (20-45° C.) is shown with grey shading. The average hot water temperature in the system was 55.3° C., with a hot water temperature drop across the system observed at 5.2-7.2° C. Potable cold and hot water in the building was sampled at 16 points throughout the building and analyzed for cATP concentrations on three separate dates. Of the 16 sampling points, only five were within the range of temperature considered to be safe for microbiological control in the absence of secondary disinfection. The remaining 11 points showed temperatures within the optimal growth range for *Legionella* (20-45° C.). More than two thirds of the analyzed samples were within ranges indicating that light biofilm was present. One sample was within the range where biofilm is present and immediate corrective action is recommended.

The measured pH values included in FIG. 6 were high, but more were still generally within the expected range for potable drinking water (pH=6 to 8.5). It was recommended that steps be taken to reduce the risk of *Legionella* contamination due to water temperatures. While increasing the hot water temperature is one such possible step, it should be noted that some cold water sample points also had temperatures high enough to be within the optimal growth range for *Legionella*. This suggests the presence of hot spots within the system where cold water plumbing is under the influence of external heat sources. These heat sources could include proximity to un-insulated hot water plumbing. Therefore, risk reduction measures in lieu of or in addition to adjustments made to the hot water temperature were strongly recommended.

Example 2—*Legionella* Control in an Assisted Living Building

A study was done on an assisted living facility building to control and remediate high levels of *Legionella* in the premise plumbing system. The temperature of the hot water system was measured and reduced over time to observe the correlation between slightly lower hot water temps and microbiological control under the stabilized peroxide based disinfection system for the premise plumbing. At certain intervals the system was flushed as part of a risk management protocol. This regular flushing of no-flow or low flow hots spots in the plumbing system ensures that disinfectant can reach all areas of the system to control microbiological growth in locations in the system that may provide opportune environments for biofilm growth. This study was a follow-up test from earlier work to further confirm findings that adequate microbiological control could be accomplished with controlled disinfectant levels, even at lower hot water temperatures. Testing was done for *Legionella pneumophila* serotype 2.

FIG. 7 is a data table showing microbiological control in the assisted living facility building. The water temperature was measured at each testing cycle. *Legionella* levels were tested at each of two locations during the duration of the study (Shower 1, Shower 2). *Legionella* tests on the water were done by culturing the water sample and sequestering for *Legionella pneumophila* serotypes 2-15, and reported in colony forming units per litre of water (cfu/L). Concentration of hydrogen peroxide concentration in the water was measured and reported in ppm or mg/L In the baseline period there was no peroxide in the water system and *Legionella* levels were concerningly high at one of the two shower locations. The system was then retrofitted with an apparatus for measuring and dosing stabilized hydrogen peroxide into the system and for monitoring system temperature, as herein described. Dosing of stabilized hydrogen peroxide into the system had an immediate effect on reduction of *Legionella* growth in the system, which remained controlled throughout the study with 7-8 ppm residual concentration of hydrogen peroxide in the water supply. A reduction in warm water temperature had no observable effect on *Legionella* growth rates with these residual levels the hydrogen peroxide.

Example 3—Energy and Water Savings

In the present system which uses stabilized hydrogen peroxide as a disinfectant, residual concentration of disinfectant can be accurately measured and maintained such that the water heater is no longer required for microbiological control or disinfection as required in solely chlorine based disinfection systems. Reliable disinfection can be achieved with stabilized hydrogen peroxide, which shifts the function of the water heater to serving only to heat water to a temperature required to provide hot water to the plumbing system and thus enable overall lowering of the heating temperature. As hot water at the site of delivery should be less than 50° C. to prevent scalding, the hot water temperature can be significantly reduced, providing energy savings and optimizing the water energy matrix. Accurate and reliable microbiological load measurement and control provides additional confidence to system operators that water will remain safe.

Figure 8:
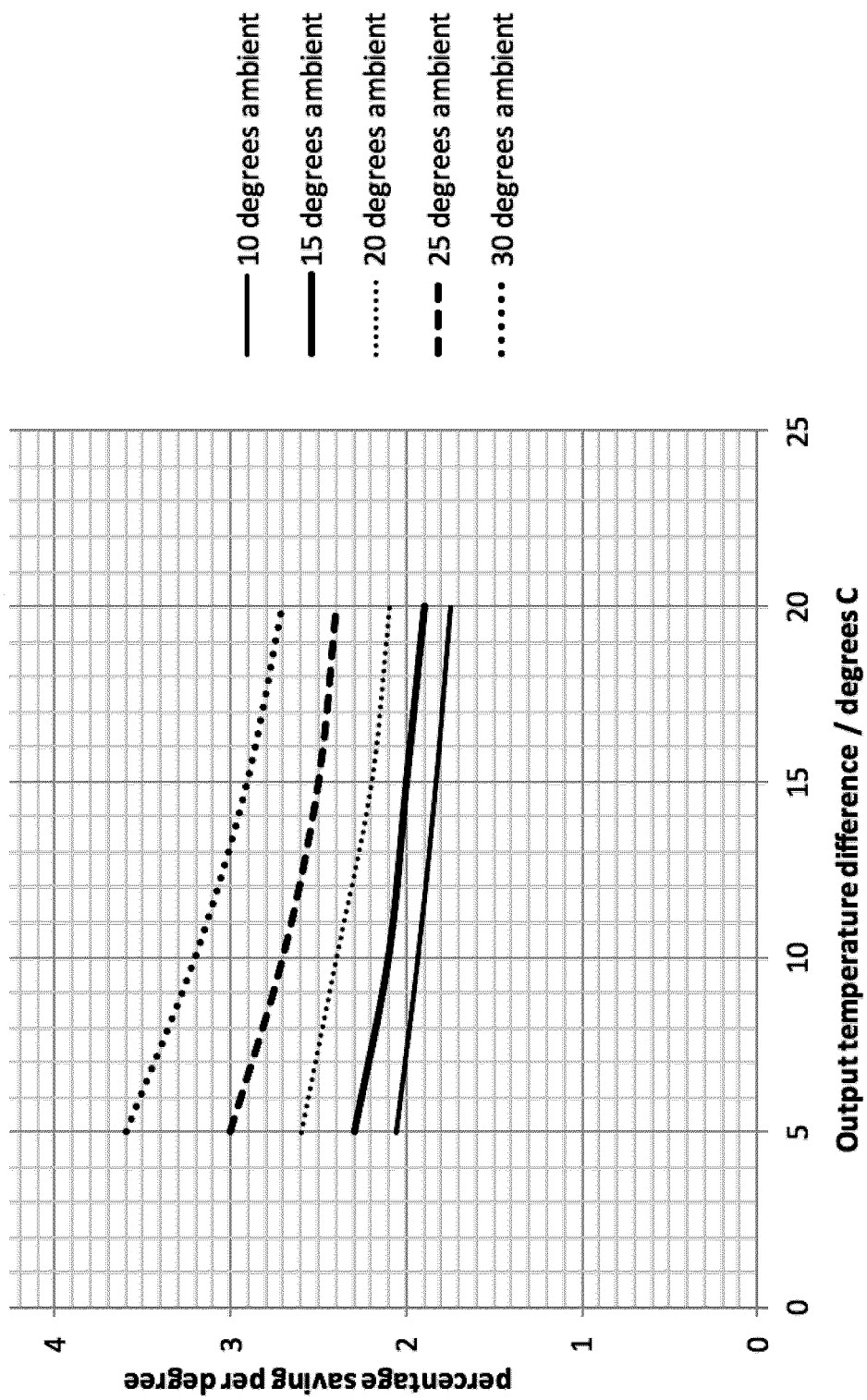
FIG. 8 is a graph of energy savings by temperature differential in a building hot water system.

FIG. 8 is a graph of energy savings by temperature differential in a building hot water system. The percentage savings on energy required for water heating that can be gained depends on the difference in outlet temperatures before and after treatment and on the ambient temperature. An approximate cost savings for energy use resulting from temperature reduction of water heating is evaluated below with natural gas as the heating energy source, based on the building described in Example 1. In this building the water usage is 5400 m$^3$/year, or 5400 tonnes/year. In a conventional chlorine-only disinfection system, if water enters the building at 13.6° C. (ambient) and is then heated to 60° C.:

Heat capacity of water=4.187 kJ/kg=4187 kJ/tonne for every 1° C.

For 46.4° C. rise, energy required is =194277 kJ/tonne (1 J=2.78×10E-7 kWh)

194277 kJ/tonne for 46.4° C. rise=54.0 kWh/tonne
54.0 kWh/tonne*5400 tonne=291648 kWh
1020 BTU/ft$^3$ natural gas=36026 BTU/m$^3$
1 kWh=3414 BTU
36026 BTU/m$^3$=10.55 kWh/m$^3$
So, 291648 kWh/10.55 kWh/m$^3$=27645 m$^3$ of natural gas needed Approximate cost of gas=$0.225862/m$^3$ (Union Gas Limited, Jul. 1, 2014) 27645 m$^3$ of natural gas*$0.225862/m$^3$=$6,243.82

Therefore, it would cost $6,243.82 to heat 5400 tonnes of water from 13.6° C. to 60° C.

In a recirculated hot water system, assuming a flow of 8 tonnes of water per hour, with water going out at 60° C. and returning at 50° C.:

93 kWh would be required to raise 8 tonnes of water 10° C.

Hourly cost=$1.99 per hour=$17,463.55 per year
Total cost per year=$6,244+$17,464=$23,707

In contrast, in a water energy matrix where the water temperature is only heated to 50° C. in a case where stabilized hydrogen peroxide disinfection is used, a significant energy savings can be gained. If water comes into the building at 13.6° C. (ambient) and is then heated to 50° C.:

4187 kJ/tonne for every 1° C. rise=152407 kJ/tonne
For 36.4° C. rise=42 kWh/tonne for 34.2° C.
42 kWh/tonne*5400 tonnes water=228793 kWh for the 36.4° C. rise
228793 kWh/10.55 kWh/m$^3$=21687 m$^3$ of natural gas needed
21687 m$^3$*$0.225862/m$^3$=$4,898

Therefore, it would cost $4,898 to heat 5400 tonnes of water from 13.6° C. to 50° C.

In a recirculated hot water system, assuming a flow of 8 tonnes of water per hour, with water going out at 50° C. and returning at 43° C.:

8.2 kWh would be required to raise 8 tonnes of water 7° C.

Every hour=$1.40 per hour=$12,225 per year
Total cost per year=$4,898+$12,225=$17,123

Therefore, the savings would be $6,584 per year to lower the temperature of the hot water heater from 60° C. to 50° C., or a 32% savings. If the water heater temperature was further lowered from 50° C. to 45° C., which is an acceptable hot water faucet temperature for user delivery, the savings would be an additional $4165.54 per year (additional 28%). It has further been found that there is a reduction in water flushing requirement of the premise plumbing system as a result of a more stable peroxide residual in the distribution system compared to chlorine alone, which results not only in savings of water, but also savings in energy required to operate the pumps, not included in the above calculation. Other benefits can be gained to municipal drinking water practice in terms of energy and water saving, infrastructure preservation, as well as its positive social impacts to human health and environmental sustainability. Other observed savings have been linked to reduced flushing and water wasted in municipal systems; less water treated with less energy demand, less chemical and infrastructure use.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

We claim:

1. A method for water energy matrix control in a hot water system, the method comprising:
   heating water in the hot water system at a temperature below a threshold temperature required for thermal disinfection;
   dosing the water system with stabilized hydrogen peroxide to maintain the concentration of stabilized hydrogen peroxide at a minimal threshold concentration of at least 1 ppm;
   monitoring concentration of stabilized hydrogen peroxide in the hot water system to maintain the concentration of stabilized hydrogen peroxide at a minimal threshold concentration of at least 1 ppm;

monitoring microbiological growth in the hot water system by measuring concentration of ATP, detection of microbiological DNA, or a combination thereof; and monitoring temperature in the hot water system to maintain the water system below a threshold temperature for thermal disinfection, wherein the stabilized hydrogen peroxide provides microbiological control in the hot water system without thermal disinfection through water heating.

2. The method of claim 1, wherein the threshold temperature in the water system is less than 60° C.

3. The method of claim 1, further comprising monitoring microbiological growth at multiple locations in the water system.

4. The method of claim 1, further comprising dosing the water system with additional stabilized hydrogen peroxide when microbiological growth is detected.

5. The method of claim 1, wherein the concentration of hydrogen peroxide in the hot water system is measured accurate to 0.1 mg/L.

6. A premise plumbing system comprising:

a water heater with temperature controller for maintaining the water heater below a threshold temperature for thermal disinfection;

a dosing pump for dosing stabilized hydrogen peroxide into the premise plumbing system;

an in-line apparatus for measuring the concentration of hydrogen peroxide at different locations in the premise plumbing system;

a temperature sensor for measuring temperature of water in the premise plumbing system downstream the water heater;

a control system for receiving hydrogen peroxide concentration data from the in-line apparatus and controlling the dosing pump based on the hydrogen peroxide concentration in the premise plumbing system; and a network of pipes connecting the water heater, dosing pump, control system, in-line apparatus and temperature sensor, wherein the control system maintains an acceptable residual concentration of hydrogen peroxide of at least 1 ppm in the premise plumbing system.

7. The system of claim 6, wherein the threshold temperature is less than 60° C.

8. The system of claim 6, wherein the network of pipes comprises a recirculating hot water loop.

9. The system of claim 6, further comprising one or more of an ATP sensor, a pH sensor, and a water flow sensor.

10. A method for reducing energy use in a potable water premise plumbing system, the method comprising:

heating water in the premise plumbing system at a temperature below a threshold temperature required for thermal disinfection;

dosing the water in the premise plumbing system with stabilized hydrogen peroxide to maintain the concentration of stabilized hydrogen peroxide at a minimal threshold concentration of at least 1 ppm;

periodically measuring, in-line, a residual concentration of hydrogen peroxide at at least one location in the premise plumbing system;

controlling a dosing pump to maintain a minimum residual concentration of hydrogen peroxide in the premise plumbing system at the minimal threshold concentration; and maintaining temperature of the water heater at a temperature of less than 60° C.

11. The method of claim 10, further comprising:

measuring a flow rate of water in the premise plumbing system; and calculating an estimated required amount of stabilized hydrogen peroxide required to maintain a minimum residual concentration of hydrogen peroxide in the premise plumbing system based on the flow rate.

12. The method of claim 10, further comprising dosing stabilized hydrogen peroxide at multiple locations in the premise plumbing system.

13. The method of claim 10, wherein the in-line measuring of the residual concentration of hydrogen peroxide occurs at multiple locations in the premise plumbing system.

14. The method of claim 10, further comprising:

measuring microbiological load in the premise plumbing system at a location distant from the site of stabilized hydrogen peroxide dosing;

periodically remeasuring the residual concentration of hydrogen peroxide in the premise plumbing system at a location distant from the stabilized hydrogen peroxide dosing location; and remeasuring the microbiological load in the premise plumbing system at a location distant from the dosing location to ensure that microbiological growth is controlled.

15. The method of claim 14, wherein measuring microbiological load comprises measuring a concentration of cellular ATP in the potable water.

* * * * *